(12) United States Patent
Magalhães Mendes

(10) Patent No.: US 9,498,765 B2
(45) Date of Patent: Nov. 22, 2016

(54) HYDROGEN OR OXYGEN ELECTROCHEMICAL PUMPING CATALYTIC MEMBRANE REACTOR AND ITS APPLICATIONS

(75) Inventor: Adélio Miguel Magalhães Mendes, Porto (PT)

(73) Assignee: CUF-QUIMICOS INDUSTRIAIS S.A., Estarreja (PT)

( * ) Notice: Subject to any disclaimer, the term of this patent is extended or adjusted under 35 U.S.C. 154(b) by 16 days.

(21) Appl. No.: 13/508,542

(22) PCT Filed: Nov. 5, 2010

(86) PCT No.: PCT/IB2010/055045
§ 371 (c)(1),
(2), (4) Date: Jul. 17, 2012

(87) PCT Pub. No.: WO2011/055343
PCT Pub. Date: May 12, 2011

(65) Prior Publication Data
US 2012/0273366 A1    Nov. 1, 2012

(30) Foreign Application Priority Data
Nov. 6, 2009    (PT) ........................................ 104812

(51) Int. Cl.
*C25B 9/00*    (2006.01)
*C25B 9/10*    (2006.01)
(Continued)

(52) U.S. Cl.
CPC .......... *B01J 19/2475* (2013.01); *C07C 209/02* (2013.01); *H01M 4/9016* (2013.01);
(Continued)

(58) Field of Classification Search
CPC ............. C25B 9/00; C25B 9/08; C25B 9/10; C25B 9/16; C25D 17/00; C25D 17/10; C25D 17/002; C25C 7/04; C25C 7/02
USPC .................................................. 204/252, 242
See application file for complete search history.

(56) References Cited

U.S. PATENT DOCUMENTS 3,919,155 A    11/1975    Squire
3,929,889 A    12/1975    Squire
(Continued)

FOREIGN PATENT DOCUMENTS

| | | | |
|---|---|---|---|
| AU | 2007340313 | * 7/2008 | .............. H01M 4/90 |
| DE | 42 35 125 A1 | 4/1994 | |
| GB | 2 203 446 A | 10/1988 | |

OTHER PUBLICATIONS

International Search Report for PCT/IB2010/055045 dated Apr. 18, 2011.

*Primary Examiner* — Zulmariam Mendez
(74) *Attorney, Agent, or Firm* — John P. White; Cooper & Dunham LLP

(57) ABSTRACT

The disclosed subject matter includes a new type of chemical reactor, described as hydrogen or oxygen electrochemical pumping catalytic membrane reactor. This new type of reactor is suitable for increasing the selectivity and the conversion rate of dehydrogenation, hydrogenation, deoxidation and oxidation reactions and namely in the direct amination reaction of hydrocarbons. This reactor can be used for the production of several chemical compounds, such as the direct amination of hydrocarbons and in particular for the synthesis of aniline from benzene. The disclosed subject matter includes a device and process wherein hydrogen is removed by electrochemical pumping of the hydrogen formed or by oxygen pumping so, as hydrogen is formed, it is oxidized. This new reactor exhibits benzene to aniline conversion higher than 40%.

18 Claims, 2 Drawing Sheets

(51) Int. Cl.
*C25B 9/08* (2006.01)
*C25B 9/16* (2006.01)
*C25D 17/00* (2006.01)
*C25D 17/10* (2006.01)
*C25C 7/04* (2006.01)
*C25C 7/02* (2006.01)
*B01J 19/24* (2006.01)
*C07C 209/02* (2006.01)
*H01M 4/90* (2006.01)
*H01M 4/92* (2006.01)
*H01M 4/94* (2006.01)
*H01M 8/06* (2016.01)
*H01M 8/08* (2016.01)
*H01M 8/00* (2016.01)
*H01M 8/10* (2016.01)
*H01M 8/12* (2016.01)

(52) U.S. Cl.
CPC ............... *H01M 4/921* (2013.01); *H01M 4/94* (2013.01); *H01M 8/0681* (2013.01); *H01M 8/086* (2013.01); *H01M 8/004* (2013.01); *H01M 8/103* (2013.01); *H01M 2008/1293* (2013.01); *H01M 2250/00* (2013.01); *Y02E 60/50* (2013.01); *Y02E 60/525* (2013.01); *Y02P 70/56* (2015.11)

(56) References Cited

U.S. PATENT DOCUMENTS

| | | | |
|---|---|---|---|
| 4,001,260 A | 1/1977 | Del Pesco | |
| 4,031,106 A | 6/1977 | Del Pesco | |
| 5,525,436 A * | 6/1996 | Savinell et al. | 429/493 |
| 2007/0082255 A1 | 4/2007 | Sun et al. | |
| 2008/0146846 A1 | 6/2008 | Dialer et al. | |
| 2009/0023956 A1 | 1/2009 | van Laar et al. | |
| 2009/0071841 A1* | 3/2009 | Pal et al. | 205/638 |
| 2009/0075149 A1 | 3/2009 | Haile et al. | |
| 2009/0127094 A1* | 5/2009 | Botte | 204/157.52 |
| 2009/0203941 A1 | 8/2009 | Laar et al. | |
| 2011/0048962 A1* | 3/2011 | Reece et al. | 205/633 |

* cited by examiner

HYDROGEN OR OXYGEN ELECTROCHEMICAL PUMPING CATALYTIC MEMBRANE REACTOR AND ITS APPLICATIONS

CROSS REFERENCE TO RELATED APPLICATIONS

This application is a U.S. national phase filing under 35 U.S.C. §371 of PCT Application No. PCT/PT2010/055045, filed Nov. 5, 2010, which in turn claims priority under 35 U.S.C. §119 to Portuguese Patent Application No. PT104812, filed Nov. 6, 2009, which applications are expressly incorporated herein by reference in their entirety.

BACKGROUND

1. Field

The disclosed subject matter relates to a hydrogen or oxygen electrochemical pumping catalytic membrane reactor, whose purpose is to increase the conversion and/or the selectivity of hydrogenation, dehydrogenation, deoxidation and oxidation reactions, both in liquid or gas phases.

The disclosed subject matter also relates to the use of a hydrogen or oxygen electrochemical pumping catalytic membrane reactor for the direct amination of hydrocarbons, particularly for the conversion of benzene into aniline, by reacting it with ammonia.

2. Related Art

The use of electrochemical pumping of hydrogen or oxygen is described in the open literature concerning systems related with energy production such as fuel cells. In the case of hydrogen, electrochemical pumping is present in polymeric membrane electrolyte fuel cells or "PEMFC," wherein the oxidation reaction on the cathode causes hydrogen permeation, under protonic form, from the anode to the cathode. On the other hand, in solid oxide fuel cell or "SOFC," the electrochemical reaction causes ionic oxygen to go from the cathode to the anode.

The literature also describes chemical reactions that may be undertaken with advantage in reactors with electrochemical pumping of hydrogen or oxygen. These systems are known as electrochemical membrane reactors and are described generally, for example in Marcano, S. and Tsotsis, T., "Catalytic Membranes and Membrane Reactors", Wiley-VCH, Chapter 2, 2002. However, it was never considered before the use of said reactors for the direct amination reactions of hydrocarbons and namely the direct amination reaction of benzene to aniline.

This direct amination reaction of benzene was first proposed in 1917 by Wibaut, as mentioned in, for example, Dialer, H.; Frauenkron, M.; Evers, H.; Schwab, E.; Melder, Johann-Peter; Rosowski, F.; Van Laar, F.; Anders, Joachim-Thierry; Crone, S.; Mackenroth, W.; Direct amination of hydrocarbons. U.S. Patent Application Publication No. 2008/0146846 A1, 2008. Ever since, many efforts have been developed to improve the conversion rate of this reaction, which is limited by the thermodynamic equilibrium.

U.S. Patent Application Publication No. 2009/0023956 describes several advances achieved. One of the most successful approaches was achieved by Dupont, whose description can be found in Documents U.S. Pat. No. 3,919,155, U.S. Pat. No. 3,929,889, U.S. Pat. No. 4,001,260 and U.S. Pat. No. 4,031,106, revealing the use of a Ni/NiO catalyst, wherein structural oxygen is used to oxidize the hydrogen formed. Both the catalyst and the process, however, present difficulties as far as the catalyst regeneration is concerned, as well as the maximum conversion that can be achieved is lower than 13% when working at 300° C. and 300 bars.

More recently, U.S. Patent Application Publication Nos. 2009/0023956 and 2009/0203941 generally disclose the addition of oxidizing gases to the reactor and the use of a suitable catalyst for the internal oxidation of hydrogen to water. Those publications also generally describe the use of a catalytic membrane reactor with a palladium or a palladium alloy membrane to carry out the direct amination reaction of benzene. A process is described, wherein hydrogen is removed from the reacting medium owing to the partial pressure difference between the retentate side (reacting medium) and the permeate side, wherein a sweep gas current is applied. This system enables the improvement of the benzene to aniline conversion up to 20% of conversion.

SUMMARY

This disclosed subject matter relates to an electrochemical catalytic membrane reactor, which increases the yield of direct amination reactions of hydrocarbons by electrochemical pumping of oxygen and/or hydrogen.

One aspect of the disclosed subject matter includes an electrochemical catalytic membrane reactor able to electrochemically pump hydrogen and/or oxygen.

One embodiment of the disclosed subject matter includes an electrochemical catalytic membrane reactor able to electrochemically pump hydrogen, and at least a composite membrane, the membrane including: (a) two electrodes, an anode (3) and a cathode (1), sandwiching an electrolyte (2); (b) both the anode (3) and the cathode (1) are electrically conductive; (c) the electrolyte (2) does not conduct electricity and forms a layer that is selective to protons; and (d) a suitable chemical catalyst (4), covering or impregnating the anode (3), preferably as a nanoparticles.

The composite membrane can also include an electrochemical catalyst which is suitable for oxidizing hydrogen, so as the resulting protons are able to permeate the electrolyte, and a second electrochemical catalyst suitable to receive protons and to reduce them, or to bring them into reaction with oxygen. In such embodiment(s), the electrochemical catalysts are preferably present in interfaces anode (3)/electrolyte (2) and/or cathode (1)/electrolyte (2).

The electrochemical catalyst on the anode side can be deposited as nanoparticles, decorating the chemical catalyst, i.e., deposited on the chemical catalyst surface (4).

In another embodiment, the hydrogen permeated through the composite membrane can be oxidized to water on the cathode (1) electrode, by adding at least one gas injector (or gas feeder) in the permeated side (i.e., in the cathode (1) side), the fed gas should include oxygen. This oxidation, which is catalyzed by an oxidation catalyst or an electrochemical catalyst deposited on the cathode, and/or at the interface with the electrolyte, such as, for example, nanoparticles of platinum, enables the generation of an electric current, which in turn can help or even be enough for the electrical pumping of hydrogen, so totally or partly avoiding the need of a voltage difference being established, which otherwise would be necessary for the electrochemical pumping of hydrogen.

In another embodiment, the catalytic membrane reactor with electrochemical pumping of hydrogen can further include at least one power supply, for generating an electrical voltage difference between both electrodes, this voltage difference can, for example, be 0.5 V.

In another embodiment, the electrode can be in contact with the reacting medium, the anode (3), can be palladium or a palladium and silver alloy, which can form a porous or dense film, permeable to hydrogen. In the case of a dense film, the chemical catalyst can be applied on the anode and the electrochemical catalyst can be applied in the anode (3)/electrolyte (2) interface.

In another embodiment, the cathode electrode (1), can be of a dense palladium layer, porous palladium or another material being electrically conductive and permeable to hydrogen.

In another embodiment, the composite membrane, known as MEA (membrane electrode assembly) can be supported on a ceramic or metallic membrane.

In another embodiment, the operating temperatures of the catalytic reactors with membrane, with electrochemical pumping of hydrogen or oxygen, may range to approximately 600° C., preferably from approximately 200° C. to approximately 500° C. if electrolyte (2) is made of yttrium-doped zirconium phosphate.

In another embodiment, the electrolyte (2) may be a polybenzimidazole membrane (PBI) doped with phosphoric acid and the operating temperature could range from approximately 120° C. to approximately 200° C.

The disclosed subject matter further includes a catalytic membrane reactor capable of the electrochemical pumping of oxygen and at least one composite membrane, the membrane including: (a) two electrodes, an anode (3) and a cathode (1) sandwiching an electrolyte (2); (b) both anode (3) and cathode (1) are electrically conductive; (c) the electrolyte (2) is non-conductive and is permeable to anionic oxygen, i.e., it forms a layer that is selective to anionic oxygen; (d) a catalyst (4), suitable for the chemical reaction and being impregnated in the anode (3), preferably as a nanoparticles; (e) at least one gas injector (or gas feeder) in the cathode (1) side, the fed gas including oxygen.

The composite membrane can also include an electrochemical catalyst suitable for oxidizing oxygen ions emerging from the electrolyte, and an electrochemical catalyst suitable to reduce oxygen to anionic oxygen before penetrating into the electrolyte. In one embodiment the electrochemical catalysts are present in interfaces anode (3)/electrolyte (2) and/or cathode (1)/electrolyte (2) or doping the anode (3) and the cathode (1).

When on the anode side, the catalyst can be the same catalyst used in the chemical reaction. So, as soon as hydrogen is formed as a result of the amination chemical reaction it reacts with the oxygen supplied by electropermeation.

In one embodiment as soon as permeated oxygen reacts with hydrogen coming from the chemical reaction, inside the reactor, an electrical potential difference arises, and the potential difference may be enough for the electrochemical oxygen pumping and so it will be not necessary to use an external electrical potential difference.

In another embodiment the catalytic reactor with membrane capable of the electrochemical pumping of oxygen, also includes a power supply, which applies an electrical potential difference between both electrodes, for example by providing a potential difference ranging from approximately 0.25 to approximately 1.5 V, or approximately 0.5 V, so as to control feeding of oxygen to the reactor.

In another embodiment, the electrolyte (2) may include a yttrium-doped zirconium oxide (YSZ).

In another embodiment, the composite membrane can include three layers, wherein: (a) the porous anode (3) may be a nickel and zirconium oxide cermet, stabilized with yttrium oxide; (b) the electrolyte (2) may be YSZ; and (c) the cathode (1) may be lanthanum strontium manganite.

In another embodiment, the composite membrane may be a typical solid oxide fuel cell (SOFC) membrane.

In another embodiment, the operating temperatures of the above-mentioned catalytic membrane reactors, capable of the electrochemical pumping of oxygen, range from approximately 500° C. to approximately 1000° C. or from approximately 600° C. to approximately 1000° C.

In another embodiment, the gas fed into the catalytic membrane reactor with electrochemical pumping of oxygen, includes air.

The above-described reactors may be used for the direct amination reaction of hydrocarbons, such as, for example, the benzene amination reaction for aniline production.

In another embodiment, the above-described electrochemical pumping catalytic membrane reactors, capable of hydrogen or oxygen electrochemical pumping, may include an assembly of tubular composite membranes. These membranes may include the amination reaction catalyst as nanoparticles, on their inner surface or impregnated in the anode.

As previously mentioned, the membrane can have a suitable structure enabling the electrochemical pumping of the resulting hydrogen from the reacting medium and its permeation either to permeate side or to a cathode electrocatalyst where the permeating hydrogen will react with oxygen to produce water and electrical potential difference for pumping hydrogen towards to the cathode.

The disclosed subject also includes a method for the direct amination of hydrocarbons, preferably benzene for aniline production, by reacting it with ammonia, in one of previously described catalytic reactors with membrane and includes the following steps: (a) the use of a catalytic reactor with membrane, working at the operation temperature and pressure; (b) the introduction of a hydrocarbon and ammonia flow in the presence of a catalyst; (c) the removal of the hydrogen formed in the reaction, by pumping hydrogen or oxygen, such that the membrane should enable the electrochemical pumping of hydrogen formed or the electrochemical pumping of oxygen to the catalyst surface.

In another embodiment, both hydrocarbon and ammonia flows are introduced in stoichiometric amounts.

In another embodiment the ammonia flow includes amounts above the stoichiometric amount.

BRIEF DESCRIPTION OF THE DRAWINGS

The accompanying drawings, which are included to provide a further understanding of the presently disclosed subject matter and are incorporated in and constitute a part of this specification, illustrate embodiments of the presently disclosed subject matter and together with the description serve to explain the principles of the presently disclosed subject matter. In the drawings.

DETAILED DESCRIPTION

Figure 1:
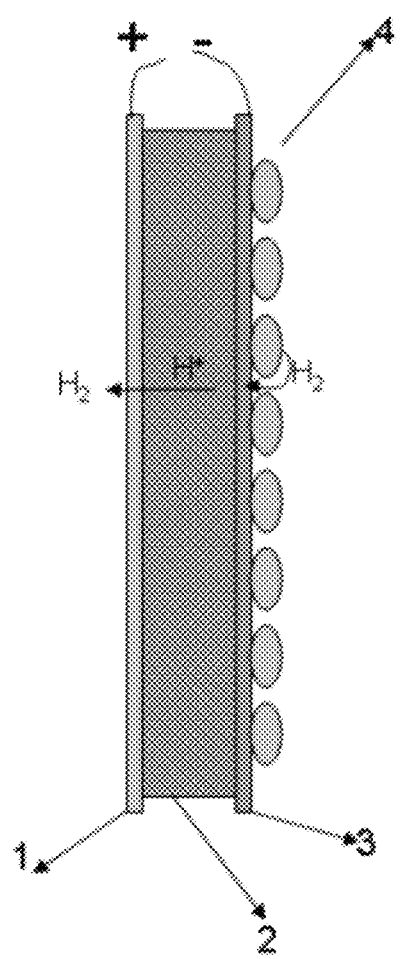
FIG. 1 illustrates a schematic representation of a composite membrane for a catalytic reactor with electrochemical pumping of hydrogen, wherein: (1)—is the cathode; (2)—is the electrolyte; (3)—is the electrode in contact with the reacting medium—the anode; (4)—is the catalyst.
Figure 2:
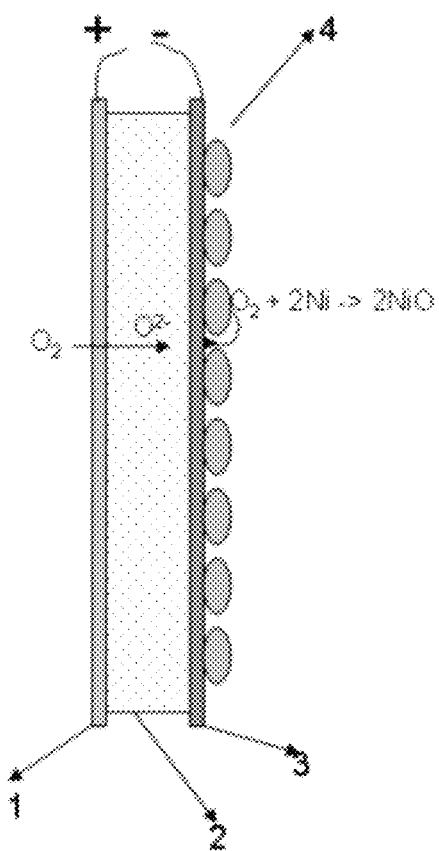
FIG. 2 illustrates a schematic representation of a composite membrane for a catalytic reactor with electrochemical pumping of oxygen and reoxidation of the nickel catalyst, wherein: (1)—is the cathode; (2)—is the electrolyte; (3)—is the electrode in contact with the reacting medium—the anode; (4)—is the catalyst.

The electrochemical pumping of hydrogen or oxygen enables, respectively, the removal or the delivery of these reagents on the chemical catalyst surface. The hydrogen removal from the chemical catalyst surface, as soon as this is formed as a result of the direct amination reaction, enables a reaction equilibrium shift towards the products. In the case of the direct amination reaction of benzene, this pumping enables a benzene conversion above 40%.

Dehydrogenation reactions are a very important class of chemical reactions that can benefit from this new technology. The direct feeding of oxygen to the catalyst surface not only improves the reaction conversion rate, since it reacts with the hydrogen formed, but it also improves the selectivity of the reaction.

When the catalytic reactor with electrochemical pumping of hydrogen or oxygen, herein described, is used, a high conversion of benzene into aniline is achieved, by using: (a) the electrochemical pumping of hydrogen—by removing hydrogen from the chemical catalyst surface; (b) the electrochemical pumping of oxygen—by feeding oxygen to the catalyst surface, forcing oxygen to immediately react with formed hydrogen and improving the benzene conversion rate, and avoiding oxidation and by-products occurrence in the reacting medium, which is the case when oxygen is directly added to the reacting medium.

At present, aniline is typically synthesized from benzene in a reactive method with two steps: the reaction of benzene with nitric acid producing nitrobenzene, and the reaction of nitrobenzene with hydrogen to produce aniline. Aniline can also be synthesized from phenol or from chlorobenzene.

The disclosed subject matter includes the use of electrochemical pumping of hydrogen or oxygen, in a catalytic membrane reactor, in order to increase the conversion rate of a chemical reaction occurring in the reactor and/or the selectivity of a direct amination of hydrocarbons.

The disclosed subject matter includes the electrochemical pumping of hydrogen or oxygen to the catalyst surface, wherein the chemical reaction takes place, improving the amination reaction conversion and selectivity. The selectivity as well as conversion improvement achieved owing to direct removal of hydrogen from the catalyst surface, where the reaction takes place. This hydrogen removal can be obtained by the electrochemical pumping of hydrogen from the catalyst surface or by the electrochemical pumping of oxygen to the catalyst surface, where it reacts with hydrogen and water is formed. For this reaction the chemical catalyst may need to be modified, for example, by decorating the same with a suitable electrochemical catalyst. When electrochemical pumping of hydrogen is used, the electrocatalyst may consist of or include platinum, and when electrochemical pumping of oxygen is used, the electrocatalyst may consist of or include nickel, which simultaneously acts as a chemical catalyst.

The catalytic membrane reactor, with electrochemical pumping of hydrogen or oxygen, makes use of a composite membrane, with can include three layers, the inner layer being a suitable electrolyte (2) and the two external layers being the electrodes. The chemical and/or electrochemical catalysts can be deposited on the electrodes or in the interface between the electrode and the electrolyte. The exact electrocatalyst localization depends on whether the electrodes allow the existence of an ionic transport between the electrocatalysts surface and the electrolyte.

In the case of hydrogen, the external layers or the electrodes can be electrically conductive, to collect the electrons formed at or to delivery electrons at the electrocatalyst, and may consist of or include palladium and/or a palladium and silver alloy. The cathode, i.e., the external layer, may consist of or include a porous metallic layer. The electrolyte can be conductive to protons and should be selected according to the reactor operating temperature, and may be a polymer, for example, a perfluorated polymer such as Nafion (for temperatures up to approximately 90° C.), or phosphoric acid doped polybenzymidazol (for temperatures between approximately 120° C. to approximately 200° C.), or it can be yttrium doped zirconium phosphate ceramics (for temperatures between approximately 200° C. to approximately 600° C.). The reactor membrane can further be supported over, for example, a sintered stainless steel membrane. Applying an electrical potential difference between the conductive layers will cause the hydrogen to permeate from inside the reactor to the outside. If oxygen or a gas mixture including oxygen is present at the cathode side, this can be used to promote a redox reaction, which in turn causes an electrical potential difference necessary to the hydrogen permeation to arise. For example, in the case of the direct amination reaction of benzene, the hydrogen permeation by electrochemical pumping can be accomplished through the hydrogen oxidation at the cathode side. This redox reaction, which can be catalyzed by platinum nanoparticles deposited in the interface between the electrolyte (2) and the cathode (1), causes a potential difference up to 1 V to arise. This potential difference causes the hydrogen permeation according to a process similar to the one occurring inside a PEMFC.

The oxygen permeation into the chemical reactor, caused by electrochemical pumping, can also be achieved by the redox reaction with the hydrogen formed inside the reactor. In those cases, the application of an external electric potential bias is minimized and may be not necessary at all.

The electrochemical catalysts can be deposited at the surfaces of the electrolyte, to enable the resulting ions (both protons and oxygen ions) to migrate to inside the electrolyte. They can also be impregnated in the electrodes if an ionic bridge with protons or oxygen anions, from or into the electrolyte is used. On the other hand, the electrocatalysts can be deposited close to the chemical catalyst, so the resulting hydrogen can be removed or the permeated oxygen can be added. In one embodiment the electrochemical catalyst in nanoparticles form can be deposited decorating the chemical catalyst. The electric current conduction will be provided by the electrodes. These should enable reagents to have free access to the chemical catalyst, both on the anode and on the cathode.

In embodiments where the electrocatalyst is deposited in the interface between the anode and the electrolyte and the chemical catalyst is deposited on the anode, hydrogen transport can be made more efficient when the chemical reaction catalyst is decorated with palladium. This metal makes the hydrogen transport from the catalyst surface to the membrane surface easier.

The oxygen electrochemical pumping can occur at temperatures within the range from approximately 500° C. to approximately 1000° C. Even in the case of oxygen electrochemical pumping, the membrane reactor can consist of or include three layers: (i) the porous anode (3), which consists of or includes, for example, an electrically conductive yttrium stabilized nickel and zirconia cermet (YSZ) layer; (ii) the electrolyte (2), forming a non-electrically conductive dense layer, for example a YSZ layer, which is selective to oxygen; and (iii) the cathode, consisting of or including, for example, an electrically conductive lanthanum strontium manganite (LSM) layer. By applying an electrical potential difference to the electrodes it is possible to control the amount of oxygen added to the reaction medium. Oxygen under ionic form ($O^{2-}$) goes through the electrolyte (2). When oxygen is added to the reacting medium, where hydrogen is formed, e.g., in the case of the direct amination reaction of benzene, it reacts with hydrogen, so creating an electrical potential difference, similarly to a fuel cell. In this case, external electrical potential bias need becomes minimized and may in some embodiments not be necessary at all.

In other embodiments, the oxygen feeding may be controlled by applying a suitable electrical potential to the electrochemical pumping catalytic membrane reactor. Oxygen is delivered directly into the chemical catalyst. This membrane is similar to those used in solid oxide fuel cells (SOFC) and may consist of or include three layers: (i) the porous anode (3), which consists of or includes, for example, an electrically conductive layer of yttrium stabilized nickel and zirconia cermet (YSZ); (ii) the electrolyte (2), forming a non-electrically conductive dense layer, for example an YSZ layer, which is selective to oxygen ions; and (iii) the cathode, consisting of or including, for example, an electrically conductive lanthanum strontium manganite (LSM).

The catalysts for the direct amination of benzene are broadly described in the literature. However, the nickel-based catalysts are generally the most active ones. Nickel use has two advantages: it can be used in the anode (3) as a catalyst for the amination reaction and as an element necessary to this layer. A nickel catalyst, decorated with palladium and/or platinum, can also be used, in order to enable the adsorption of the hydrogen formed during the amination and its further catalytic oxidation with permeated oxygen.

Accordingly, the electrochemical pumping of oxygen is essential for removing the hydrogen formed and to improve the conversion and the selectivity of said amination reaction. On the other hand, it also enables the continuous regeneration of structural oxygen from the nickel catalyst, through direct supply of oxygen to the catalyst. This process minimizes the production of by-products, which are formed with oxygen is added directly to the reactor feeding flow.

This reactor operates at a temperature between approximately 500° C. and approximately 1000° C., which is the temperature range wherein the electrolyte (2) is conductive to oxygen ions.

EXAMPLES

Examples are given below to more fully illustrate the presently disclosed subject matter, and should not be construed as limiting the invention.

It will be apparent to those skilled in the art that various modifications and variations can be made in the presently disclosed subject matter and specific examples provided herein without departing from the spirit or scope of the invention. Thus, it is intended that the invention covers the modifications and variations of this presently disclosed subject matter that come within the scope of any claims and their equivalents.

The following examples are for illustrative purposes only and are not intended, nor should they be interpreted, to limit the scope of the invention.

Example 1

In one embodiment, a catalytic reactor with a membrane can be equipped with an electrochemical oxygen pump such as a composite catalytic membrane, wherein the catalyst for the direct amination reaction of benzene is a bimetallic catalyst that includes nickel/nickel oxide and platinum nanoparticles; the electrocatalyst in the permeate side is a catalyst with platinum nanoparticles; the porous anode (3) consists of or includes, for example, a nickel and zirconium oxide cermet, stabilized with yttrium oxide (YSZ); the cathode (1) consists of or includes, for example, lanthanum strontium manganite (LSM); the electrolyte (2) is yttrium-doped zirconium phosphate.

Example 2

In another embodiment, an electrocatalytic pumping catalytic membrane reactor, wherein hydrogen can be removed from the chemical catalyst surface, includes an electrochemical hydrogen pump that includes a nickel/nickel oxide chemical catalyst to provide the direct amination reaction of benzene to aniline. The hydrogen pump/catalyst can further include platinum nanoparticles, which can in turn provide the hydrogen electro-oxidation. The composite catalyst should be deposited in the interface between the anode (3) and the electrolyte (2); the anode (3) can, for example, be a porous palladium membrane with a thickness of approximately a 1 µm; the electrolyte (2) can be, for example, a yttrium-doped zirconium phosphate; the cathode (1) can, for example, be a porous palladium membrane with a thickness of approximately 0.5 µm. In the interface, the electrolyte (2)/cathode can be deposited with platinum electrocatalyst as nanoparticles. This is intended either to provide the hydrogen reduction, or its reaction with oxygen.

Example 3

In another embodiment, an electrocatalytic pumping catalytic membrane reactor, wherein oxygen is electrochemically pumped to the chemical catalyst surface, can include a nickel/nickel oxide chemical catalyst to provide the direct amination reaction of benzene and the oxygen electro-oxidation. This composite membrane can be made of (i) a porous YSZ anode (3) impregnated with the nickel/nickel oxide catalyst; (ii) impermeable YSZ electrolyte (2) layer; and (iii) lanthanum strontium manganite (LSM) cathode (1) layer.

Although the presently disclosed subject matter has been described and illustrated with a certain degree of particularity, it is understood that the disclosure has been made only by way of example, and that numerous changes in the conditions and order of steps can be resorted to by those skilled in the art without departing from the spirit and scope of the invention.

The invention claimed is:

1. A catalytic membrane reactor comprising:
   (a) an electrically conductive anode comprising a cermet made of an electrically conductive layer of nickel and a proton conductive layer;
   (b) an electrically conductive cathode;
   (c) an non-electrically conductive electrolyte located between said anode and said cathode that forms a layer selective to protons;
   (d) a chemical catalyst located at at least one of (i) an outer surface of said anode and (ii) another surface of the anode which is disposed between said anode and said electrolyte and is disposed opposite to the outer surface, wherein the chemical catalyst is a nickel catalyst consisting of a single metal element which is constituted by nickel, and the nickel catalyst is decorated with nanoparticles of platinum or palladium deposited on a surface of the nickel catalyst;
   (e) a first electrocatalyst capable of oxidizing hydrogen deposited on at least one of (i) the chemical catalyst, to decorate the chemical catalyst, and (ii) a surface of the anode opposite to the chemical catalyst; and (f) a second electrocatalyst capable of reducing hydrogen located at or near at least one of (i) said cathode and (ii) an interface between said cathode and said electrolyte, wherein said first and second electrocatalyst are the same or a different material, and wherein said reactor has an operating temperature range of between approximately 500° C. and approximately 1000° C.

2. The catalytic membrane reactor of claim 1, further comprising a power supply that applies an electrical potential difference between said electrodes.

3. The catalytic membrane reactor of claim 1, further comprising
(g) a gas supply providing gas to said cathode, wherein said gas comprises oxygen.

4. The catalytic membrane reactor of claim 1, further comprising a power supply that applies an electrical potential difference between said anode and said cathode.

5. The catalytic membrane reactor of claim 1, wherein said anode is porous.

6. The catalytic membrane reactor of claim 1, wherein said anode comprises at least one of palladium, platinum, a silver alloy and combinations thereof.

7. The catalytic membrane reactor of claim 1, wherein said cathode comprises at least one of palladium, porous palladium layer and combinations thereof.

8. The catalytic membrane reactor of claim 1, wherein said catalytic membrane reactor is supported on at least one of a ceramic material, a metallic porous membrane material and combinations thereof.

9. The catalytic membrane reactor of claim 1, wherein said catalytic membrane reactor has a working temperature of up to approximately 600° C.

10. A catalytic membrane reactor equipped with a composite membrane and capable of electrochemically pumping oxygen comprising:
(a) an electrically conductive anode comprising a cermet made of an electrically conductive layer of nickel and an ion conductive layer of yttria-stabilized zirconia (YSZ);
(b) an electrically conductive cathode comprising an electrically conductive layer of lanthanum strontium manganite;
(c) an non-electrically conductive electrolyte that is selective to anionic oxygen located between said anode and said cathode that forms a layer selective to oxygen ions;
(d) a chemical catalyst located in or on a surface of said anode, wherein the chemical catalyst is a nickel catalyst consisting of a single metal element which is constituted by nickel, and the nickel catalyst is decorated with nanoparticles of platinum or palladium deposited on the surface of the nickel catalyst;
(e) a gas supply providing gas to an area of said catalytic membrane reactor at or near said cathode, wherein said gas comprises oxygen;
(f) a first electrocatalyst capable of oxidizing hydrogen deposited on at least one of (i) the chemical catalyst to decorate the chemical catalyst, and (ii) a surface of the anode opposite the chemical catalyst; and
(g) a second electrocatalyst capable of reducing oxygen located at or near at least one of (i) said cathode and (ii) an interface between said cathode and said electrolyte wherein said first and second electrocatalyst are the same or a different material; and wherein said reactor has an operating temperature range of between approximately 500° C. and approximately 1000° C.

11. The catalytic membrane reactor of claim 10, further comprising a power supply that applies an electrical potential difference between said anode and said cathode.

12. The catalytic membrane reactor of claim 10, wherein said composite membrane is a solid oxide fuel cell membrane.

13. The catalytic membrane reactor of claim 10, wherein said gas comprises air.

14. The catalytic membrane reactor of claim 10, wherein said catalytic membrane reactor comprises a bundle of more than one tubular composite membranes.

15. A method for the direct amination reaction of hydrocarbons using the catalytic membrane reactor of claim 1 comprising:
(a) providing a hydrocarbon;
(b) providing ammonia
(c) removing any hydrogen produced by the reaction of said hydrocarbon and said ammonia, wherein said hydrogen is electrochemically pumped to said catalyst located at or near at least one of (i) said anode and (ii) an interface between said anode and said electrolyte and wherein said hydrogen is oxidized.

16. The method of claim 15, wherein said hydrocarbon and said ammonia are provided in stoichiometric proportions.

17. The method of claim 15, wherein said ammonia provided stoichiometrically exceeds said hydrocarbon provided.

18. The method of claim 15, wherein said hydrocarbon provided comprises one of benzene and the product of the reaction is a substituted benzene compound.

* * * * *